United States Patent [19]

Harders et al.

[11] 4,289,649

[45] Sep. 15, 1981

[54] AQUEOUS LIPID STANDARD SOLUTION

[75] Inventors: Hans-Dieter Harders; Roland Helger, both of Darmstadt, Fed. Rep. of Germany

[73] Assignee: Merck Patent Gesellschaft mit beschränkter Haftung, Darmstadt, Fed. Rep. of Germany

[21] Appl. No.: 74,457

[22] Filed: Sep. 11, 1979

[30] Foreign Application Priority Data

Sep. 11, 1978 [DE] Fed. Rep. of Germany ....... 2839433

[51] Int. Cl.$^3$ .................... C09K 3/00; G01N 33/48
[52] U.S. Cl. .................... 252/408; 23/230 B; 23/909
[58] Field of Search .............. 252/408; 23/230 B, 909; 435/11

[56] References Cited

U.S. PATENT DOCUMENTS

| | | | |
|---|---|---|---|
| 2,185,969 | 1/1940 | Schultze | 424/101 |
| 3,260,648 | 7/1966 | Fox | 252/408 |
| 3,754,865 | 8/1973 | Gindler | 23/230 B |
| 3,853,465 | 12/1974 | Rush et al. | 252/408 |
| 3,859,047 | 1/1975 | Klein | 252/408 |
| 3,891,573 | 6/1975 | Stary et al. | 252/408 |
| 4,011,045 | 3/1977 | Bonderman | 252/408 |
| 4,040,784 | 8/1977 | Deshmukh | 23/230 B |
| 4,042,330 | 8/1977 | Deshmukh | 23/230 B |
| 4,066,508 | 1/1978 | Rauscher et al. | 23/230 B |
| 4,184,848 | 1/1980 | Batz et al. | 252/408 |
| 4,189,400 | 2/1980 | Proksch et al. | 252/408 |

OTHER PUBLICATIONS

Chong-Kit, R., et al., Clin. Chem., vol. 20, No. 11, pp. 1454–1457, (1974).
Vass, L., Arztl. Lab., vol. 20, pp. 148–151, (1974).

*Primary Examiner*—Teddy S. Gron
*Attorney, Agent, or Firm*—Millen & White

[57] ABSTRACT

A stable, aqueous, substantially alcohol-free lipid standard solution, comprising water, at least one lipid, and an effective lipid-solubilizing amount of both a non-ionic detergent and an ionic detergent. A simple, convenient method for making such a solution is provided.

13 Claims, No Drawings

AQUEOUS LIPID STANDARD SOLUTION

BACKGROUND OF THE INVENTION

This invention relates to an aqueous lipid standard solution which comprises water, a lipid and both an ionic and a non-ionic detergent.

Clinical chemical measurements as a rule require standard solutions, the properties of which should as closely as possible resemble those of a serum. For this purpose, the particular substance must be dissolved in an aqueous system, since only in this way will the standard sample behave like a serum. In addition, such a standard solution should not change over a lengthy period of time. These requirements are particularly difficult to meet in the case of standard solutions for the determination of lipids, e.g., cholesterol or triglycerides.

In addition to organic solvents for preparing solutions of cholesterol, the literature describes the following aqueous solvent systems for this purpose; aqueous solutions of cholesterol and non-ionic detergents are described in German Auslegeschrift 1,523,133 and in Arztl. Lab. 20, 148–151 (1974); and water-alcohol mixtures of cholesterol with added detergents are described in German Auslegeschrift No. 2,324,386. Standard solutions prepared with non-ionic detergents are stable for only a few weeks, particularly with cholesterol concentrations within the pathological range. Because of their alcohol content, standard solutions with added alcohol evaporate substantially more than does a serum sample, even if relatively high-boiling alcohols are used. Lowering the alcohol content causes the lipid to precipitate. This cannot be cured by increasing the detergent concentration since this results in an undesirably high viscosity, which can interfere with metering.

A need therefore continues to exist for a lipid standard solution which is free of the aforementioned disadvantages.

OBJECTS OF THE INVENTION

It is an object of this invention to provide a substantially alcohol-free, stable, aqueous lipid standard solution which resembles a serum as closely as possible, evaporates as little as possible if the samples unavoidably have to stand, and has a viscosity which does not interfere with metering.

Another object of the invention is to provide a simple and convenient method of preparing such a standard solution.

Upon further study of the specification and appended claims, further objects and advantages of this invention will become apparent to those skilled in the art.

SUMMARY OF THE INVENTION

According to the invention, the foregoing objects have been achieved by providing a stable, aqueous, substantially alcohol-free lipid standard solution which comprises at least one lipid and both a non-ionic detergent and an ionic detergent.

DETAILED DISCUSSION

It has been found, surprisingly, that it is possible to prepare an alcohol-free, stable, aqueous lipid standard solution if, in addition to a non-ionic detergent such as one of those disclosed in the aforementioned publications, an ionic detergent is used at a relatively high concentration of 0.5–10% by weight. The solvent power of these mixtures is then so good that even cholesterol esters of long-chain ($C_{12-22}$) fatty acids, which esters are the form in which cholesterol is predominantly present in the serum, can be kept in solution though they are substantially less polar and less water-soluble than free cholesterol. It is also possible, by means of the invention, to bring into solution other lipids, the determination of which is of clinical importance, such as triglycerides, lecithin and the like.

The aqueous lipid standard solution according to the invention contains, in addition to 0.2–4 g/l of cholesterol and/or 0.1–2 g/l of a triglyceride such as triolein, about 2–20% by weight, preferably 5–15% by weight, of non-ionic detergent and, furthermore, about 0.5–10% by weight, preferably 1–5% by weight, of an ionic detergent.

The non-ionic detergents which may be used to prepare the lipid standard solution of the invention broadly include any water soluble, lipid solubilizing non-ionic surface active agent.

Suitable such non-ionic detergents include condensation products of an alcohol, phenol, or an alkyl phenol with from 2 to about 15 ethylene oxide units to form a monoalkyl, monophenyl or mono-alkylphenyl ether of a polyethylene glycol. Typical, non-limitative examples include diethylene glycol monobutyl ether, hydroxypolyethoxydodecane and octylphenoxypolyethoxyethanol. Also suitable are the polyethoxyethylenesorbitan fatty acid esters, such as "Tweens", and the like.

Preferred non-ionic detergents are the polyethylene glycol mono-alkylphenyl ethers, including the "Triton X 100" ethers with 8–12 ethylene glycol units on an alkylphenol. The alkylphenols are typically made by condensing olefins such as isobutylene and a phenol.

The ionic detergents which may be used to prepare the novel lipid standard solution are either cationic or anionic detergents.

Suitable cationic detergents include but are not limited to quaternary ammonium halides such as alkylbenzyldimethylammonium chlorides (alkyl is preferably $C_{8-18}$), (alkylbenzyl) trimethylammonium chlorides (alkyl is preferably $C_{8-24}$), methylbenzethonium chloride, and the like.

Suitable anionic detergents include but are not limited to alkali metal salts, preferably sodium salts, of alkylaryl sulfonic acids, alkyl sulfuric and phosphoric acids, aminoalkyl and amidoalkyl sulfonic, sulfuric and carboxylic acids, acyloxy and alkoxy sulfonic and sulfuric acids, and the like. Suitable examples include sodium dioctylsulfosuccinate, sodium triisopropylnaphthalenesulfonate, sodium dodecylsulfate and sodium N-lauroylsarcosinate.

The standard solution can in addition contain other lipids of clinical importance, such as cholesterol esters of long-chain (e.g., $C_{12-22}$) fatty acids (0.1–2 g/l) and/or lecithin (0.2–4 g/l). If necessary, the pH value of the standard solution can be brought to the range of 6–8 by means of a buffer. Suitable buffers include but are not limited to tris, phosphate, triethanolamine or imidazole buffers, in a concentration of 10–100 millimol/l. The use of a tris-HCl buffer of pH 7.4, at a concentration of 20 millimols/l, is preferred. To avoid microbial contamination, 0.5–20 g/l of a conventional antimicrobial agent such as an alkali metal azide, preferably 1 g/l of sodium azide, can also be added.

In the past, lipid standard solutions or emulsions have been prepared by ultrasonic treatment or by cautiously and slowly diluting a mixture of cholesterol and detergent with water. The former method requires expensive technical equipment, and procedural safety measures, while the latter requires considerable care when adding the water, in order to avoid precipitation of the cholesterol.

These advantages can be circumvented if the lipid standard solution is prepared by a simple one-pot, two-step sequence. First, the lipids and the detergents are dissolved in an inert, volatile organic solvent to achieve thorough mixing of these components. The solvent is then evaporated off under reduced pressure and the requisite amount of water is added, optionally with slight warming, whereupon solution is rapidly effected. The water can additionally contain an antimicrobial agent such as an alkali metal azide, and a buffer.

Suitable volatile organic solvents include any inert organic solvent or mixture of solvents capable of substantially dissolving both the lipid and the detergent components, and having a boiling point, at atmospheric pressure, lower than 100° C., preferably lower than 70° C. Suitable such solvents include lower alcohols halogenated alkanes, esters, and the like. Preferred solvents include methylene chloride and methanol.

Standard lipid solutions according to the present invention contain the lipids as a micellar solution; they are stable for prolonged periods of time, normally not less than about 12 weeks.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

300 mg of cholesterol, 200 mg of cholesterol linolate, 200 mg of triolein, 100 mg of lecithin, 5 g of polyethylene glycol mono-[p-(1,1,3,3-tetramethylbutyl)phenyl] ether (8-12 ethoxy units) and 1 g of sodium dioctylsulfosuccinate are dissolved in 25 ml of methylene chloride. The methylene chloride is evaporated off under reduced pressure and the residue is taken up with 80 ml. of water at about 40° C.; after the mixture has cooled, it is made up to 100 ml with water. A clear, stable lipid standard solution is obtained.

EXAMPLE 2

300 mg of cholesterol, 5 g of polyethylene glycol monooctylphenyl ether (8-12 ethoxy units) and 1 g of sodium dodecylsulfate are dissolved in 25 ml of methylene chloride. The methylene chloride is evaporated off under reduced pressure and the residue is taken up with water, and made up to the appropriate volume, as described in Example 1. A clear, stable standard solution is produced.

EXAMPLE 3

300 mg of cholesterol, 200 mg of cholesterol linolate, 200 mg of triolein, 10 g of polyethylene glycol monooctylphenyl ether and 5 g of alkylbenzyldimethylammonium chloride (average molecular weight 365) are dissolved in 25 ml of methanol. The alcohol is evaporated off under reduced pressure and the residue is taken up with water, and made up to the appropriate volume, as described in Example 1. A clear, stable standard solution is produced.

EXAMPLE 4

300 mg of cholesterol, 5 g of polyethylene glycol monooctylphenyl ether and 2 g of methylbenzethonium chloride are dissolved in 25 ml of methanol. The alcohol is evaporated off under reduced pressure and the residue is taken up with 80 ml. of warm tris-HCl buffer (20 millimol/l; pH 7.4), which additionally contains 1 g/l of sodium azide, and, after cooling, is made up to 100 ml with the same solution.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A stable, aqueous, substantially alcohol-free lipid standard solution, comprising water, at least one lipid, and an effective lipid-solubilizing amount of both a non-ionic detergent and an ionic detergent; wherein the amount of ionic detergent is from 0.5 to 10% by weight and the amount of the non-ionic detergent is from 2 to 20% by weight.

2. The lipid standard solution of claim 1, wherein said amount of ionic detergent is from 1 to 5% by weight.

3. The lipid standard solution of claim 1, wherein said amount of non-ionic detergent is from 5 to 15% by weight.

4. The lipid standard solution of claim 1, wherein said lipid is at least one of cholesterol, a triglyceride, lecithin and the cholesterol ester of a $C_{12-22}$ fatty acid.

5. The lipid standard solution of claim 4, wherein the lipid is cholesterol, in an amount of from 0.2 to 4 grams per liter of solution.

6. The lipid standard solution of claim 4, wherein the lipid is a triglyceride, in an amount of from 0.1 to 2 grams per liter of solution.

7. The lipid standard solution of claim 6, wherein said triglyceride is triolein.

8. The lipid standard solution of claim 1, wherein the non-ionic detergent is selected from polyethylene glycol monoalkyl ethers, polyethylene glycol mono-alkylphenyl ethers and polyoxyethylene-sorbitan fatty acid esters.

9. The lipid standard solution of claim 1, wherein the non-ionic detergent is polyethylene glycol monooctyl or mono-[p-(1,1,3,3-tetramethylbutyl)phenyl] ether, said ether having 8-12 ethoxy units in the polyethylene glycol moiety.

10. The lipid standard solution of claim 1, wherein the ionic detergent is an alkylbenzyldimethylammonium chloride or methylbenzethonium chloride.

11. The lipid standard solution of claim 1, wherein the ionic detergent is selected from sodium dioctylsulfosuccinate, sodium triisopropylnaphthalenesulfonate, sodium dodecylsulfate and sodium N-lauroylsarcosinate.

12. The lipid standard solution of claim 1, which further contains at least one of a buffer and an alkali metal azide.

13. The lipid standard solution of claim 1, wherein said ionic detergent is an anionic detergent.